United States Patent [19]
Kanda

[11] Patent Number: 5,968,918
[45] Date of Patent: Oct. 19, 1999

[54] METHOD FOR THE PREVENTION OF CORONARY ARTERY SPASM

[76] Inventor: Iwao Kanda, 1617 Via Margarita, Rancho Pales Verdes Estates, Calif. 40206

[21] Appl. No.: 08/953,340

[22] Filed: Oct. 17, 1997

[51] Int. Cl.⁶ .................................................. A61K 31/58
[52] U.S. Cl. ...................... 514/176; 514/177; 514/178; 514/369; 514/652
[58] Field of Search .................................. 514/176, 177, 514/178, 652, 369

[56] References Cited

U.S. PATENT DOCUMENTS

| | | | |
|---|---|---|---|
| 4,729,999 | 3/1988 | Young | 514/227 |
| 5,472,985 | 12/1995 | Grainger et al. | 514/651 |
| 5,512,557 | 4/1996 | Collins | 514/170 |
| 5,733,925 | 3/1998 | Knuz et al. | 514/449 |

OTHER PUBLICATIONS

I. Kanda, M. Endo Coronary Artery Spasm: a Hypothesis on Prevention by Progesterone, *Medical Hypothesis*, 49, 183–185, Aug. 1997.

*Primary Examiner*—James H. Reamer
*Attorney, Agent, or Firm*—John E. Vanderburgh

[57] ABSTRACT

The present invention relates to the prevention of coronary artery spasm in mammals by the administration of an effective amount of an antiestrogen compound to block estrogen receptors for the reduction or prevention of the formation of an estrogen—estrogen receptor complex so that estrogen response elements in the DNA of the smooth muscle of the coronary arteries is not activated by the complex. The method of the invention is used to reduce the risk of spasm induced cardiac problems such as sudden infant death syndrome. The antiestrogen is selected from the group consisting of progestins and nonsteroidal antiestrogen compounds.

10 Claims, No Drawings

METHOD FOR THE PREVENTION OF CORONARY ARTERY SPASM

FIELD OF THE INVENTION

This invention relates to a method to reduce the incidence of coronary artery spasm and atherogenesis and more particularly, a method of treatment involving the administration of an effective amount of a compound having antiestrogen properties.

BACKGROUND

Sudden Infant Death Syndrome (SIDS) is a medical term that describes the sudden death of an infant which remains unexplained after all known and possible causes have been carefully ruled out through autopsy, death scene investigation, and review of the medical history. Nearly 90% of the deaths occur in the first six months of life.

There has been much study into the causes of Sudden infant Death Syndrome (SIDS)in recent years. Incidences of this tragic syndrome have received wide publicity and many studies of SIDS have been conducted. Pediatricians and others studying the syndrome have emphasized the placement of the infant in its crib in an attempt to prevent the onset of SIDS. Many hypotheses have been formulated and presented as to the cause of the syndrome, including such causes as choking and asphyxiation from lack of oxygen. Accordingly, conventional wisdom now is to place an infant on its back to decease the incidence of SIDS which has met with limited success. Even so, SIDS continues to occur among infants for no apparent reason and, to date there is no consensus as to the cause of SIDS.

There are other unexplained incidences of nocturnal death in young adults as well as in infants which exhibit characteristics similar to SIDS. For example, in Asia sudden unexpected death during sleep has been reported among young Asian and Oceanian males around the age of 25. This syndrome, which is named Sudden Unexpected Nocturnal Death syndrome (SUNDS) is also known as Pokkuri Disease in Japan and Bangungut in the Philippines. SUNDS rarely occurs in menstruating females and SUNDS among Caucasians is rare as compared to Asian and Oceanian populations but does occur occasionally. See for example, R. Myerburg *Sudden Death*. The Heart, McGraw, Hill, New York, 1978, page 732.Sudden unexplained death among older Japanese males around age 40, during sleep is also sufficiently common as to have been named "Karoshi" (dying from exhaustion).

SUMMARY OF THE INVENTION

The foregoing syndromes, as well as other sudden unexpected coronary incidents, which may occur without warning and usually without evidence of coronary disease with certain individuals, are believed to be due to coronary artery spasms (CAS) usually occurring at a site of coronary arthersclerosis. A CAS incident is believed to be brought on by estrogen reacting on active estrogen receptors in the smooth muscle of the coronary arteries of certain individuals.

In accordance with the present invention, the reduction of estrogen receptors in the smooth muscle of coronary arteries is accomplished by the administration of a therapeutic composition comprising, in admixture with a pharmaceutically acceptable carrier, an effective amount of an antiestrogen to reduce or block estrogen receptors in the smooth muscle of the coronary arteries. Although the mechanism involved is not fully understood at this time, reduction of estrogen receptors decreases the occurrence of a CAS incident and the resultant coronary damage incurred thereby. For example, due to the severe contraction of the smooth muscle, caused by a CAS incident, the smooth muscle at the location of the CAS incident can be torn precipitating coronary thrombosis.

DETAILED DESCRIPTION OF THE INVENTION

A Coronary Artery Spasm (CAS) is the cause of a variety of coronary problems which can prove to be fatal. A CAS produces a contraction of the vessels which substantially cuts down, or completely blocks, the normal flow of blood to the heart producing an infarct or other necrosis of arterial tissue and heart muscle. Infants aged 2–5 months experiencing a CAS may develop myocardial infarctions which by age 7 months present as endocardia fibroelastosis with old inferio-lateral myocardial infarction which can lead to congestive heart failure. This has been studied and reported by A. Moore and E. Lambert *Endocardia Fibro Elastosis, Pediatric Cardiology*, 733 (1968). As reported by Moore et al., the origin of the Endocardia fibroelastosis with old inferio-lateral myocardial infarction may be a response to some primary myocardial dysfunction due to a number of differing etiological functions. In their autopsied patients, they observed extensive necrosis and scarring of the lateral and inferior walls of the left ventricle associated with thinning of the myocardium. The coronary arteries were usually normal and there was no demonstrable coronary arterial disease.

In the case of SUNDS, pathological studies of sudden and unexpected death, i.e. autopsies performed on victims of the unexplained cardiac death showed no evidence of myocardial infarction or of atherosclerosis. M. Sugai, *Acta Pathol. Jap.*, 9:273 (1959) and J.Cruz, *The Pathology of "Bangungul"*. *Jour. P. M. A.*, Vol. XXXVII, 7, 476–4. Similarly, juvenile myocardia infarction and Prinzmetal's angina pectoris associated with normal coronary arteries is found among young Japanese males within the age distribution population for SUNDS.

Although there are many possible causes for the diseases and coronary problems discussed above, one cause which is known to cause any of the foregoing is coronary artery spasm (CAS), also sometimes referred to as vasospasm. This can decrease or even stop the flow of blood to a part of the heart. A CAS incident can occur in a normal coronary artery as well as in one that is partly blocked due to atherosclerosis. When the spasm occurs, the person can experience chest pain called angina pectoris. The spasm may typically occur during rest rather than during periods of exertion. If the spasm is severe, it is possible that a heart attack could occur. The reasons for spasm are unclear.

In the case of SIDS, and SUNDS, CAS is targeted as a cause of the unexplained incidents. For example, SIDS may be the result of a spasm of the right coronary artery due to the activation of the smooth muscle of the proximal portion of the right coronary artery. This activation produces a spasm of the right coronary artery (R-CAS). Such a spasm can result in ventricular fibrillation causing the sudden death of the infant leaving no trace of the occurrence of the R-CAS. Similarly it appears that CAS can produce Endocardia fibroelastosis with old inferio-lateral myocardial infarction in infants as well as coronary damage leading to juvenile myocardia infarction and Prinzmetal's angina pectoris.

In seeking an initiating factor for CAS, I considered estrogen and its effect on the coronary system. I concluded that estrogen can contribute to or even be the direct cause of a CAS incident in certain infants which ultimately produces the various coronary diseases and incidents discussed above.

Estrogen is known to produce coronary incidents of various types although the effects of estrogen on the coronary system are not fully understood. However, in a study to test the safety and efficacy of several drugs for the treatment of coronary disease, the administration of 5.0 mg/day estrogen to a large group of middle aged men who had evidence of more than one myocardial infarction or who had one myocardial infarction plus complications as a result of the infarct was discontinued because that group exhibited an increase in adverse effects than in the placebo group. After 18 months of follow up, the group receiving the 5 mg/day estrogen had an excess number of myocardial infarctions and the coronary death rate was higher for that group than for the placebo group. *The Coronary Drug Project, Initial Findings Leading to Modifications of Its Research Protocol,* A, V. 214, p 1303 (Nov. 16, 1970). In a study of women using oral contraceptive comprising estrogen the incidence of coronary events was 5 times higher than for women not taking the pill. S. Shapiro, et al., *Oral Contraceptive Use in Relation to Myocardial Infarction,* Lancet, p 743–746 (April 7, 1979). The estrogen level in the umbilical artery is almost 100 times higher than the normal estrogen level in a nonpregnant female. W. Hung, G.P. August, A.M. Glasgow, *Pediatric Endocrinology,* pp. 331–332 (Medial Examination Publishing, 1978).

The role of estrogen in fetal and new born infants is believed to play an important factor in the closure of the ductus arteriosis of a new born. In that regard a newborn infant is exposed to as much as 100 times the normal concentration of estrogen in the mother's blood via the umbilical artery.

The dormant gene of the smooth muscle of the human coronary artery is identical or similar to the active gene of the smooth muscle of ductus atherosclerosis. Essentially everyone has the dormant gene although a few individuals apparently do not have the active gene. These individuals as infants did not have a normal closure of the ductus arteriosis and apparently are not at risk of an estrogen induced CAS.

The dormant gene in most individuals remains inactive but in some cases the gene is activated by estrogen, apparently because of a higher than normal number of estrogen receptors, to cause the smooth muscle to function like the smooth muscle of the ductus arteriosis and attempt to close producing a coronary arterial spasm. Thus, in these individuals, the smooth muscle of coronary arteries is highly susceptible to a CAS incident induced by estrogen because an abnormally high number of estrogen response elements present in the smooth muscle of the arteries producing activation of the normally dormant gene. Once activated, the dormant gene in the coronary artery will trigger a CAS in an attempt to close the artery as if it were the ductus atherosclerosis. For example, activation of the smooth muscle of the coronary artery in infants appears to require about 2 months from birth to produce a CAS which typically lasts for three months. This coincides with available data concerning the occurrence of SIDS in infants.

As discussed above, recognizing that an infant is exposed to very high estrogen levels (100 times greater than normal estrogen levels) through the umbilical artery and that the physiology of the smooth muscle of coronary artery is in many ways similar to that of the ductus atherosclerosis, it was determined that exposure of the smooth muscle of the coronary artery to very high levels of estrogen would, in the case of those individuals whose genetic code renders them susceptible, activate a dormant gene in the nucleus of the smooth muscle to initiate a CAS incident. For example, in the case of SIDS, a CAS incident in the right coronary artery may induce cardiac arrhythmia which can ultimately can lead to death or serious damage to cardiac tissue. In post pubescent males and in menopausal females the dormant gene in certain individuals may be activated by the hormonal changes occurring during that stage of their life thus rendering the individual susceptible to estrogen in their system. Since obviously not all infants, post pubescent males and menopausal females develop SIDS, SUNDS, myocardial infarction or other cardiac problems associated with CAS, it would appear that the tendency to CAS is dependent upon the susceptibility of the dormant gene to activation by estrogen. Unfortunately, there is no known procedure for predicting whether or not an individual will be susceptible to CAS except for the fact that a previous sibling has died of a SIDS or SUNDS incident or has developed other cardiac problems associated with CAS. This appears to be a matter of heredity and evidence does exist that multiple instances of SIDS and SUNDS occurs in certain families.

In accordance with the present invention, a method for preventing CAS caused by estrogen activation of the dormant gene in arterial smooth muscle of susceptible individuals consists of administering a pharmaceutically effective amount of a therapeutic compound comprising an antiestrogen selected from the group consisting steroidal and nonsteroidal antiestrogen compounds. As used herein the term antiestrogen is applied both to the nonsteroidal and steroidal compounds that act to block or bind the estrogen receptors in the nuclei of the smooth muscle of the coronary arteries of the recipient to prevent or reduce the formation of an estrogen-estrogen receptor complex. This complex activates the estrogen response elements in the DNA of certain individuals which induces a CAS incident..

Antiestrogen compounds and their preparation are known in the art and they are currently under investigation as therapeutic agents, for example as agents in the treatment of osteoporosis and certain types of cancer, such as breast cancer although the long term effects of antiestrogens compounds is not known. Antiestrogens useful in the present invention include steroidal compounds, referred to generally as progestins, and nonsteroidal compounds. The progestin group includes progesterone, medroxy-progesterone acetate (MPA), depo-MPA, 17 alpha-hydroxy pregnenolone, 11-alpha-hydroxy progesterone, 17-alpha-hydroxy progesterone, megestrol acetate, norethindrone, norethindrone acetate, norethynodrel, norgestrel, pregnenolone, chlormadinone acetate, clomiphene citrate, danazol, 16-dehydropregnenolone, 16-dehydropregnenolone acetate, 16-dehydro-progesterone and ethisterone. The nonsteroid compounds include tamoxifin, droloxifene and raloxifene.

The antiestrogen may be administered in combination with other therapeutic compounds to treat ancillary problems which may be associated with CAS. For example, high fasting insulin concentrations appear to be a marker of increased risk for ischemic heart disease in men (*N Engl J Med,* March 1996) and some evidence suggests that a decrease in insulin levels may have a significant benefit on long-term mortality. For example, in the presence of coronary atherosclerosis, the usual site of a CAS incident is at the site of the atherosclerosis. Hyperinsulinernia appears to play a role in atherogenesis by the proliferation of the cellular element of atherosclerosis with particular emphasis on the proliferation of medial smooth muscle into vascular lumen. This can be prevented by the enhancement of insulin receptors at fatty and muscle tissues, as well as reduction of hepatic glycogenesis so that the insulin level will be lowered. Troglitazone, distributed by Park Davis under the name Rezulin™, an insulin receptor enhancer, has been shown to reduce circulating insulin levels. *New Approaches to the Pharmacotherapy of Diabetes, Mini-symposium,* 56th Meeting of the American Diabetes Association, Jun. 9, 1996. Troglitazone can be combined with an antiestrogen to reduce the risk of ischemic disease which may accompany a CAS incident in patients suffering from Type II diabetes mellitus and impaired glucose tolerance.

Antiestrogen compounds are available in injectable and tablet form. The steroidal antiestrogens will normally be best administered by injection and this is the method of choice for infants. The non-steroidal antiestrogens are available in tablet form.

EXAMPLE I

The following describes the administration of an effective amount of progestin to a fetus to reduce the risk of a SIDS incident. The mother and fetus are chosen on the basis of a family history of SIDS or otherwise unexplained coronary problems which are associated with CAS incidents.

The antiestrogen used is an aqueous solution of medroxyprogesterone acetate (150mg/ml) distributed by Upjohn Pharmaceutical as Depo-Provera™ Contraceptive Injection. The solution is diluted with sterile water 1000 times to a concentration of the antiestrogen of 150 $\mu$g/ml prior to use. One cc of the solution is administered as a single fetal injection during the 36th to 39th week of gestation.

It is highly preferred to administer the progestin in those cases where there is a family history of a child who has died of SIDS or who has contracted coronary disease, such as endocardia fibroelastosis with old inferio-lateral myocardial infarction, which can be caused by a CAS. As pointed out above, the tendency to CAS in infants is believed to be an inherited tendency. Unfortunately, as of the date of this invention, there are no markers to predict whether a fetus has a tendency towards CAS although there is every prospect that study of the genetic code of such infants will identify the dormant gene and will provide a method for predicting the tendency for a fetus to develop CAS after birth.

EXAMPLE II

A patient on insulin therapy having Type II diabetes mellitus and having experienced a coronary incident exhibits resting chest pain and exertional chest pain indicating atherosclerosis. A CAS incident is highly probable under these circumstances. As a preventative measure 400 mg of Rezulin™ and 0.5 mg of medroxyprogesterone are administered on a daily basis. Alternatively, 10 mg of tamoxifin can be administered along with the Rezulin™ in lieu of the medroxyprogesterone. Insulin therapy is continued.

Having defined the invention I claim:

1. A method for preventing the occurrence of a coronary artery spasm by the reduction of estrogen receptors in the smooth muscle of coronary arteries comprising the administration of a therapeutic composition comprising an effective amount of an antiestrogen to prevent the activation of estrogen response elements in the smooth muscle of the coronary arteries.

2. The method of claim 1 wherein said antiestrogen is selected from the group consisting of the progestins, nonsteroidal antiestrogen compounds, the pharmaceutically acceptable salts thereof and combinations thereof.

3. The method of claim 1 wherein said antiestrogen is selected from the group of progestins consisting of progesterone, medroxy-progesterone acetate (MPA), depo-MPA, 17 alpha-hydroxy pregnenolone, 11-alpha-hydroxy progesterone, 17-alpha-hydroxy progesterone, megestrol acetate, norethindrone, norethindrone acetate, norethynodrel, norgestrel, pregnenolone, chlormadinone acetate, clomiphene citrate, danazol, 16-dehydropregnenolone, 16-dehydropregnenolone acetate, 16-dehydro-progesterone and ethisterone, progestin and combinations thereof.

4. The method of claim 1 wherein said antiestrogen is selected from the nonsteroidal antiestrogen group consisting of tamoxifin, droloxifene and raloxifene and combinations thereof.

5. The method of claim 1 wherein said antiestrogen is administered as an effective amount of a therapeutic composition comprising said antiestrogen in admixture with a pharmaceutically acceptable carrier.

6. The method of claim 1 wherein said antiestrogen is medroxyprogesterone acetate.

7. The method of claim 1 wherein said antiestrogen is administered in combination with troglitazone.

8. A method for the prevention of a CAS incident in infants, said method comprising the steps of:
   a. preparing an aqueous solution of an effective concentration of an antiestrogen selected from the group consisting of medroxyprogesterone and the pharmaceutically acceptable salts thereof; and
   b. injecting an effective amount of said solution into a fetus suspected of being susceptible to coronary artery spasm.

9. The method of claim 7 wherein the concentration of said antiestrogen in said solution is 150 $\mu$g/ml.

10. The method of claim 7 wherein said antiestrogen is administered as a single fetal injection during week 36 to week 39 of gestation.

* * * * *